US006270815B1

(12) United States Patent
Kim et al.

(10) Patent No.: US 6,270,815 B1
(45) Date of Patent: Aug. 7, 2001

(54) FERMENTATION PROCESS FOR PREPARING ERYTHRITOL USING MOTHER LIQUOR PRODUCED FROM PURIFICATION PROCESS OF PALATINOSE

(75) Inventors: Sang Yong Kim, Kyunggi-Do; Deok Kun Oh, Cheonbuk; Bong Soo Noh, Seoul; Soo Ryun Jung, Seoul; Kyung Ah Kim, Seoul, all of (KR)

(73) Assignees: Bolak Co., Ltd., Kyunggi-Do; BioNgene Co., Ltd., Seoul, both of (KR)

( * ) Notice: Subject to any disclaimer, the term of this patent is extended or adjusted under 35 U.S.C. 154(b) by 0 days.

(21) Appl. No.: 09/468,091

(22) Filed: Dec. 21, 1999

(51) Int. Cl.[7] ........................................................ C12P 7/18
(52) U.S. Cl. .......................... 426/60; 435/158; 435/255.1
(58) Field of Search ..................... 435/158, 444, 435/255.4, 254.1, 255.1; 426/7, 14, 60

(56) References Cited

U.S. PATENT DOCUMENTS 5,902,739 * 5/1999 Abe et al. ............................. 435/158
5,962,287 * 10/1999 Suh et al. ............................. 435/158

FOREIGN PATENT DOCUMENTS

136802 * 4/1985 (EP) .

OTHER PUBLICATIONS

Ishizuka et al, Journal of Fermentation . . . , vol. 68, No. 5, "Breeding of a Mutant of Aureobasidium . . . ", pp. 310–314, 1989.
Cho et al, Food Sci. Biotechnol., vol. 8, No. 2, "Effect of Osmotic Pressure of Salts on . . . ", pp. 73–77, 1999.
Yang et al, Biotechnology Letters, vol. 21, "Production of erythritol from glucose . . . ", pp. 887–890, 1999.
Hirata et al, Journal of Bioscience . . . , vol. 87, No. 5, "High–Level Production of Erythritol . . . ", pp. 630–635, 1999.
Ha jny et al, "Erythritol Production by a yeastlike fungus", *Applied Microbiology*, 12 (3): 240–246, May 1964.*

* cited by examiner

*Primary Examiner*—Keith Hendricks
(74) *Attorney, Agent, or Firm*—Jacobson Holman, PLLC

(57) ABSTRACT

The present invention relates to a fermentation process to have a high productivity with a novel mutant of Torula sp. DS101 (KCMM-10171), more specifically, for preparing erythritol using mother liquor produced from purification process, which comprises 30~60% of trehalulose, 10~30% of palatinose, 5~15% of fructose, 5~25% of glucose and 0~10% of sucrose.

5 Claims, No Drawings

US 6,270,815 B1

FERMENTATION PROCESS FOR PREPARING ERYTHRITOL USING MOTHER LIQUOR PRODUCED FROM PURIFICATION PROCESS OF PALATINOSE

BACKGROUND OF THE INVENTION

The present invention relates to a fermentation process for preparing erythritol in high productivity with a novel mutant of Torula sp. DS101, more specifically, for preparing erythritol using mother liquor produced from purification process of palatinose, which comprises 30~60% of trehalulose, 10~30% of palatinose, 5~15% of fructose, 5~25% of glucose and 0~10% of sucrose.

Erythritol is a four-carbon polyol with property similar to other polyols currently used as food ingredients, such as, xylitol, sorbitol, manintol, maltitol, lactitol and isomalt. It is a naturally occurring substance and is widely distributed in nature. Erythritol is a metabolite or storage compound for seaweed and mushrooms. Fruits like melons, grapes and pears contain erythritol. It occurs frequently in fermented foods including wines and beers, and processed vegetables, such as, soy sauce and oriental miso bean paste.

Erythritol has sweetness with 60~70% of sucrose in a 10% solution. Its high negative heat of solution provides the crystalline material with a strong cooling effect. Erythritol can be safely used in foods to make them tooth-friendly. This property causes the inability of dental caries by developing bacteria to use erythritol as a fermentation substrate. Erythritol as a small molecule has strong colligative properties, such as, strong freezing point depression, boiling point elevation and high osmotic pressure. With its low hygroscopicity and viscosity in solution, it is very useful to reduce and control the water activity of foodstuff.

Erythritol can be produced by microbial methods using the osmophilic yeasts, especially species of the genus Torulopsis such as *T. magnoliae, T. veratilis,* and *T. candida; Endonycopsis chodati; Hansenula supelliculsa; Pichia miso; Monilliella tomentosa* var. *pollinis; Trigonopsis variabilis;* Trichosporonoides; *Candida zeylanoides;* and Aureobasidium sp. *Monilliella tomentosa* var. *pollinis* on the medium containing 33~37% of glucose with 43~48% of erythritol yield. However, erythritol production using such strains could not be applied to industrial scale due to the formation of by-products, such as, glycerol and ribitol.

On the other hand, industrial production of erythritol has been performed using a mutant of Aureobasidium. The mutant was isolated and developed by cooperative study of Nikken Chemical and National Food Research Institute of Japan. The mutant produced erythritol with 1.8~1.9 g/L·h volumetric productivity and 42~44% yield in the medium containing 40% of glucose. This has been regarded as the highest report of erythritol productivity and yield among the erythritol-producing microorganisms.

It has not been previously reported that Torula sp. produces erythritol. However, the inventors found that a mutant of Torula sp. isolated from a 40% of sucrose solution produces erythritol.

SUMMARY OF THE INVENTION

An object of the present invention is to provide novel mutants cells of Torula sp. DS101, which were deposited to Korean Culture Center of Microorganism with accession number KCCM-10171 on Sep. 7, 1999 under Budapest treaty, for preparing erythritol with high productivity.

Another object of the present invention is to provide the optimal fermentation conditions for maximum production of erythritol using mutant cells of Torula sp. DS101 (KCCM-10171) by controlling following conditions;

i) fermenting the medium consisting of mother liquor produced from purification process of palatinose as carbon source, 1.8~2.2% of yeast extract as nitrogen source and 0.2~0.4% of $KH_2PO_4$ with mutant cells wherein a) said mother liquor contains 20~50% of sugar as total sugar b) pH of culture medium is 4.5~6.5;

c) temperature of cultivation is 28~38° C.

d) aeration rate of the medium is 0.1~1.0 volume of air per volume of medium per minute; and e) agitation speed of the medium is 300~1200 rpm;

ii) removing the mutant cells and other residue from the fermentation medium; and iii) separating and recovering erythritol from the fermentation medium of step (ii).

The further object of the present invention is to provide a fermentation process wherein the composition of said mother liquor comprises 30~60% of trehalulose, 10~30% of palatinose, 5~15% of fructose, 5~25% of glucose and 0~10% of sucrose.

The further object of the present invention is to provide a method of isolating Torula sp. DS101 (KCCM-10171) comprising the steps of:

i) spreading and culturing a wild type Torula sp. on growth medium (18~22% of glucose and 0.9~1.1% of yeast extract) containing 0.01% of N-methyl-N'-nitro-N-nitroguanidine FNTG);

ii) isolating the produced colonies at least three times on growth medium;

iii) spreading and culturing the colonies of step (ii) on growth medium under UV illumination of 250~270 nm; and iv) isolating the growing colonies.

DETAILED DESCRIPTION OF THE INVENTION

The mutant cells used for the present invention are isolated by following method.

Isolation of a High Erythritol Producing Mutant

A wild strain from the air in 40% sucrose solution at Bolak Co., Osan, Kyunggi-Do, Korea was selected to produce erythritol. A single colony was incubated in a 250-mL flask containing 50 mL of growth medium (18~22% of glucose and 0.9~1.1% of yeast extract). It was incubated at 28~32° C. and 230~270 rpm until the optical density of culture broth at 600 nm reached at 1.0. The grown cells were collected by centrifugation at 3,000 g for 20 min and washed with 0.1 M citrate buffer pH 5.5.

The collected cells were resuspended in the buffer solution containing 0.01% of N-methyl-N'-nitro-N-nitroguanidine (NTG) and incubated at 28~32° C. for 25~35 mmn. After NTG treatment, the cells were incubated at 28~32° C. for 8~12 hours in YM broth and plated on the agar plate containing 38~42% of glucose and 1.8~2.2% of yeast extract for the selection of a high erythritol producing mutant. Single colony was selected as fast growing mutants. The selected colony was transferred on the fermentation medium containing 18~22% of glucose and 0.9~1.1% of yeast extract to test erythritol producing activity in shake flask. After incubating at 28~32° C. and 230~270 rpm in 100~160 hours, a high erythritol producing mutant was selected and colony produced was separated by repeating separation method more than 3 times.

The obtained colony was again spread and cultured to the medium containing 18~22% of glucose and 0.9~1.1% of yeast extract under UV illumination of 250~270 nm. Finally, growing colony was isolated and obtained as mutant cells and used as strain in this invention.

This mutant has superior properties compared to the those of wild strain in erythritol yield from glucose, volumetric productivity, and sugar tolerance.

Characterization of a High Erythritol Producing Mutant

Microorganism which can produce erythritol from glucose was selected and was identified as Torula sp. Microbial characteristics of a high erythritol producing mutant are as follows;

1) Description

Cream colonies; vegetative reproduction by budding; no filamentous no sexual reproduction.

2) Fermentation

The sugar which can be used for the fermentation of such mutant is illustrated in following Table 1.

TABLE 1

| Material | Ferment. | Material | Ferment. |
|---|---|---|---|
| D-Glucose | + | Lactose | − |
| D-Galactose | − | Cellobiose | − |
| D-Mannose | + | Melezitose | − |
| D-Fructose | + | Raffinose | − |
| Maltose | − | Starch | − |
| Sucrose | + | Inulin | − |
| Trehalose | − | D-xylose | − |
| Melibiose | − | | |

\* + means can be used for fermentation,
− means cannot be used for fermentation.

3) Growth

Following materials are tested if they can be used as growth medium. Table 2 shows the result.

TABLE 2

| Material | Growth | Material | Growth |
|---|---|---|---|
| D-Glucose | + | D-Mannitol | + |
| D-Galactose | + | Galactitol | − |
| D-Mannose | + | myo-Inositol | − |
| D-Fructose | + | D-Gluconate | + |
| L-Sorbose | + | D-Glucuronate | − |
| D-Glucosamine | − | D-Galacturonate | − |
| D-Ribose | + | DL-Lactate | − |
| D-Xylose | + | Succinate | + |
| D-Arabinose | + | Citrate | + |
| L-Rhamnose | + | Methanol | − |
| Maltose | − | Ethanol | − |
| Sucrose | + | Propanediol | − |
| Palatinose | + | Nitrate | − |
| Trehalulose | + | Ethylamine | + |
| Trehalose | − | L-Lysine | + |
| Melibiose | − | Cadaverine | + |
| Salicin | + | Creatine | − |
| Arbutin | + | Creatinine | − |
| Lactose | − | Glucosamine | − |
| Cellobiose | − | Imidazole | − |
| Melezitose | − | w/o vitamins | − |
| Raffinose | − | 25° C. | + |
| Starch | − | 37° C. | + |
| Inulin | − | 40° C. | − |
| Glycerol | + | 0.01% Cycloheximide | + |
| Erythritol | − | 0.1% Cycloheximide | − |
| Ribitol | + | 1.0% Acetic acid | − |
| Xylitol | + | 50% D-Glucose | + |

TABLE 2-continued

| Material | Growth | Material | Growth |
|---|---|---|---|
| L-Arabinitol | − | 60% D-Glucose | + |
| D-Glucitol | + | 70% D-Glucose | − |

\* + means can be used for growth medium,
− means cannot be used for growth medium.

4) Additional Characteristics

Following test shows if they have specific property as to this test. Table 3 shows the result.

TABLE 3

| Test | Result | Test | Result |
|---|---|---|---|
| Starch formation | − | Urea hydrolysis | − |
| Acetic acid production | − | Diazonium Blue B reaction | − |

\* + means positive test result,
− means negative test result.

This mutant cell of Torula sp. DS101 was deposited to Korean Culture Center of Microorganism, 361-221, Yurim B/D Hongje-1-dong, Seodaemun-gu, Seoul 120-091, Republic of Korea with accession number KCCM-10171 on Sep. 7, 1999 under Budapest treaty.

Using such strain, the cultivation was performed for erythritol production. Glucose, major compound for erythritol production, contributed mainly to production cost to manufacture erythritol produced by fermentation process. In order to reduce production cost, glucose cost should be reduced. The decrease of glucose cost, however, is very difficult due to the decrease of erythritol production. If major compound for erythritol production uses by-products of purification process produced from making sugar, the production cost could significantly be reduced.

Therefore, in this invention, a wild strain of Torula sp., an isolated strain from the air in 40% sucrose solution at Bolak Co., Osan, Kyunggi-Do, Korea was selected to produce erythritol. The wild strain was mutated with N-methyl-N'-nitro-N-nitroguanidine (NTG) treatment. One of mutants has superior properties compared to the wild strain in erythritol yield from glucose, volumetric productivity and sugar tolerance.

By using the mutant of Torula sp., erythritol production was performed in the mother liquor produced from purification process of palatinose, which comprised palatinose, trehalulose, sucrose, fructose and glucose.

The present invention concerns a method of obtaining erythritol with a high yield and a high volumetric productivity in Torula sp. mutant by using mother liquor produced from purification process of palatinose.

The following is fermentation method for producing erythritol using mutants cells.

Seed Culture

A frozen (−70° C.) mutant cells of Torula sp. are cultivated in a 250-mL flask containing 50 mL growth medium at 28~32° C. and 230~270 rpm for 43~53 hours and this seed culture are transferred to a 5-L fermentor for producing erythritol in main culture.

Main Culture

The fermentation medium consists of mother liquor produced from purification process of palatinose as carbon source, 1.8~2.2% of yeast extract as nitrogen source, and 0.2~0.4% of $KH_2PO_4$. The mother liquor contains 30~60% of trehalulose, 10~30% of palatinose, 5~15% of fructose, 5~25% of glucose and 0~10% of sucrose. Cultures in the fermentor are performed at 28~38° C., pH 4.5~6.5 and aeration rate of 0.1~1.0 vvm during the fermentation. Agitation speed is gradually increased from 300 to 1,200 rpm to maintain the level of dissolved oxygen above 20% within 24 hours. After 24 hours, the agitation speed is fixed to 600 rpm.

After 100~160 hours, the amount of erythritol, fructose, glucose, palatinose, trehalulose is measured by high performance liquid chromatography (Shimadzu RID-6A, Japan) equipped with Carbohydrate analysis column (Waters, USA). Dry cell weight is estimated by using a calibration curve made from relationship between optical density at 600 nm and dry cell weight.

Finally, the fermentation medium is centrifuged for removing cells and other residue, and the supernatant is filtered and dialyzed for obtaining erythritol.

The present invention will be more specifically explained by the following examples. However, it should be understood that the examples are intended to illustrate but not in any manner to limit the scope of the present invention.

EXAMPLE 1

A frozen (−70° C.) mutant cells of Torula sp. were cultivated in a 250-mL flask containing 50 mL growth medium at 30° C. and 250 rpm for 48 hours and this seed culture was transferred to a 5-L fermentor containing 3L fermentation medium for producing erythritol. The fermentation medium consisted of sucrose as carbon source, yeast extract as nitrogen source and 0.3% of $KH_2PO_4$. Cultures in the fermentor were performed at 34° C., pH 5.5 and aeration rate of 0.5 vvm during the fermentation. Agitation speed was gradually increased from 300 to 1,200 rpm to maintain the level of dissolved oxygen above 20% within 24 hours. After 24 hours, the agitation speed was fixed to 600 rpm.

After 120 hours fermentation, the amount of erythritol from 30% of sucrose and 1.5% of yeast extract was measured by HPLC equipped with Carbohydrate analysis column. The obtained erythritol was 132 g/L and volumetric productivity was 1.07 g/L·h.

After 120 hours fermentation, the amount of erythritol from 40% of sucrose and 2.0% of yeast extract was measured by HPLC equipped with Carbohydrate analysis column. The obtained erythritol was 190 g/L and volumetric productivity was 1.58 g/L·h.

After 140 hours fermentation, the amount of erythritol from 50% of sucrose and 2.5% of yeast extract was measured by HPLC equipped with Carbohydrate analysis column. The obtained erythritol was 223 g/L and volumetric productivity was 1.55 g/L·h.

EXAMPLE 2

A frozen (−70° C.) mutant cells of Torula sp. were cultivated in a 250-mL flask containing 50 mL growth medium at 30° C. and 250 rpm for 48 hours and this seed culture was transferred to a 5-L fermentor containing 3L fermentation medium for producing erythritol. The fermentation medium consisted of palatinose as carbon source, yeast extract as nitrogen source, and 0.3% of $KH_2PO_4$. Cultures in the fermentor were performed at 34° C., pH 5.5 and aeration rate of 0.5 vvm during the fermentation. Agitation speed was gradually increased from 300 to 1,200 rpm to maintain the level of dissolved oxygen above 20% within 24 hours. After 24 hours, the agitation speed was fixed to 600 rpm.

After 120 hours fermentation, the amount of erythritol from 30% of palatinose and 1.5% of yeast extract was measured by HPLC equipped with Carbohydrate analysis column. The obtained erythritol was 110 g/L and volumetric productivity was 0.92 g/L·h.

After 120 hours fermentation, the amount of erythritol from 40% of palatinose and 2.0% of yeast extract was measured by HPLC equipped with Carbohydrate analysis column. The obtained erythritol was 160 g/L and volumetric productivity was 1.33 g/L·h.

After 140 hours fermentation, the amount of erythritol from 50% of palatinose and 2.5% of yeast extract was measured by HPLC equipped with Carbohydrate analysis column. The obtained erythritol was 180 g/L and volumetric productivity was 1.29 g/L·h.

EXAMPLE 3

A frozen (−70° C.) mutant cells of Torula sp. were cultivated in a 250-mL flask containing 50 mL growth medium at 30° C. and 250 rpm for 48 hours and this seed culture was transferred to a 5-L fermentor containing 3L fermentation medium for producing erythritol. The fermentation medium consisted of trehalulose as carbon source, yeast extract as nitrogen source, and 0.3% of $KH_2PO_4$. Cultures in the fermentor were performed at 34° C., pH 5.5 and aeration rate of 0.5 vvm during the fermentation. Agitation speed was gradually increased from 300 to 1,200 rpm to maintain the level of dissolved oxygen above 20% within 24 hours. After 24 hours, the agitation speed was fixed to 600 rpm.

After 120 hours fermentation, the amount of erythritol from 30% of trehalulose and 1.5% of yeast extract was measured by HPLC equipped with Carbohydrate analysis column. The obtained erythritol was 90 g/L and volumetric productivity was 0.75 g/L·h.

After 120 hours fermentation, the amount of erythritol from 40% of trehalulose and 2.0% of yeast extract was measured by HPLC equipped with Carbohydrate analysis column. The obtained erythritol was 140 g/L and volumetric productivity was 1.17 g/L·h.

After 140 hours fermentation, the amount of erythritol from 50% of trehalulose and 25% yeast extract was measured by HPLC equipped with Carbohydrate analysis column. The obtained erythritol was 170 g/L and volumetric productivity was 1.21 g/L·h.

EXAMPLE 4

A frozen (−70° C.) mutant cells of Torula sp. were cultivated in a 250-mL flask containing 50 mL growth medium at 30° C. and 250 rpm for 48 hours and this seed culture was transferred to a 5-L fermentor containing 3L fermentation medium for producing erythritol. The fermentation medium consisted of mother liquor produced from purification process of palatinose as carbon source, 20% extract as nitrogen source, and 0.3% of $KH_2PO_4$. The mother liquor contained 47.5% of trehalulose, 20% of palatinose, 17.5% of fructose, and 15% of glucose and its concentration was adjusted to 40% as total sugar. Culture in the fermentor were performed at 34° C., pH 5.5 and aeration rate of 0.5 vvm during the fermentation. Agitation speed was gradually increased from 300 to 1,200 rpm to maintain the level of dissolved oxygen above 20% within 24 hours. After 24 hours, the agitation speed was fixed to 600 rpm. Fermentation profiles of cell mass and erythritol production in the medium containing the mother liquor were shown Table 4.

TABLE 4

| Time (h) | Cell mass (g/L) | Erythritol (g/L) |
|---|---|---|
| 0 | 0.1 | 0 |
| 24 | 2.8 | 5.2 |
| 40 | 8.2 | 48.2 |
| 62 | 12.5 | 76.5 |
| 80 | 17.8 | 102 |
| 96 | 18.9 | 126 |
| 120 | 21.4 | 160 |

Comparative Example 1

A frozen (−70° C.) mutant cells of Torula sp. were cultivated in a 250-mL flask containing 50 mL growth medium at 30° C. and 250 rpm for 48 hours and this seed culture was transferred to a 5-L fermentor containing 3L fermentation medium for producing erythritol. The fermentation medium consisted of 40% of glucose as carbon source, 2.0% of yeast extract as nitrogen source, and 0.3% of $KH_2PO_4$. Cultures in the fermentor were performed at 34° C., Ph 5.5 and aeration rate of 0.5 vvm during the fermentation. Agitation speed was gradually increased from 300 to 1,200 rpm to maintain the level of dissolved oxygen above 20% within 24 hours. After 24 hours, the agitation speed was fixed to 600 rpm. Fermentation profiles of cell mass and erythritol production in the medium containing glucose were shown as Table 5.

TABLE 5

| Time (h) | Cell mass (g/L) | Erythritol (g/L) |
|---|---|---|
| 0 | 0.1 | 0 |
| 24 | 7.2 | 8.1 |
| 40 | 24.5 | 50.2 |
| 62 | 26.5 | 98.5 |
| 80 | 27.5 | 110 |
| 96 | 29.3 | 140 |
| 120 | 31.0 | 155 |

What is claimed is:

1. The mutant of Torula sp. DS101 which is the same as that deposited at Korean Culture Center of Microorganism and identified by accession number KCCM-10171.

2. A fermentation process for producing erythritol which comprises culturing the mutant according to claim 1, and recovering erythritol from the culture medium.

3. The fermentation process according to claim 2, which comprises culturing cells of the mutant under the following conditions:

i) fermenting the mutant cells in medium comprising a carbon source, a nitrogen source and $KH_2PO_4$;
   a) the medium having a pH of from 4.5 to 6.5;
   b) cultivating being effective at a temperature in the range of from 28 to 38° C.;
   c) the medium being aerated at a rate of from 0.1 to 1.0 volume of air per volume of medium per minute; and
   d) the medium being agitated at a speed of from 300 to 1200 rpm;

ii) removing the mutant cells and other residue from the medium; and iii) separating and recovering erythritol from the medium of step (ii).

4. The fermentation process of claim 3, wherein the carbon source is mother liquor produced from purifying palatinose, the nitrogen source is from 1.8 to 2.2% of yeast extract, and the $KH_2PO_4$ is in an amount of from 0.2 to 0.4%.

5. The fermentation process according to claim 4, wherein the medium comprises mother liquor having from 30 to 60% of trehalulose, from 10 to 30% of palatinose, from 5 to 15% of fructose, from 5 to 25% of glucose and from 0 to 10% of sucrose.

* * * * *